United States Patent
Yu et al.

(10) Patent No.: US 12,290,544 B1
(45) Date of Patent: May 6, 2025

(54) **ESSENTIAL OIL OF STEMS AND LEAVES OF *CHUZHOU CHRYSANTHEMUM* AND APPLICATION THEREOF**

(71) Applicant: Chuzhou University, Chuzhou (CN)

(72) Inventors: Shijun Yu, Chuzhou (CN); Xinyi Chai, Chuzhou (CN); Xiaoli Jia, Chuzhou (CN); Kaiqun Yin, Wuhan (CN); Ruibo Xu, Chuzhou (CN); Huan Wang, Jilin (CN); Shuang E, Nanjing (CN); Bin Han, Bozhou (CN); Qin Gao, Bozhou (CN); Longzhu Dou, Dezhou (CN); Jingyi Xia, Hefei (CN); Xin Le, Fuzhou (CN)

(73) Assignee: Chuzhou University, Chuzhou (CN)

( * ) Notice: Subject to any disclaimer, the term of this patent is extended or adjusted under 35 U.S.C. 154(b) by 0 days.

(21) Appl. No.: 18/934,450

(22) Filed: Nov. 1, 2024

(30) Foreign Application Priority Data

Nov. 3, 2023 (CN) .......................... 202311456151.3

(51) Int. Cl.
*A61K 36/287* (2006.01)
*A61P 31/04* (2006.01)

(52) U.S. Cl.
CPC ............ *A61K 36/287* (2013.01); *A61P 31/04* (2018.01); *A61K 2236/15* (2013.01); *A61K 2236/31* (2013.01); *A61K 2236/331* (2013.01); *A61K 2236/37* (2013.01); *A61K 2236/55* (2013.01)

(58) Field of Classification Search
None
See application file for complete search history.

(56) References Cited

FOREIGN PATENT DOCUMENTS

| | | | |
|---|---|---|---|
| CN | 102726458 A | 10/2012 | |

OTHER PUBLICATIONS

Yan (CN 112680279 A—English translation) Apr. 20, 2021.*
Liu Baohua et al., "Experimental Study on Anti-Inflammatory Effect of *Chrysanthemum morifolium* Volatile Oil", Chemistry and Bioengineering, 2015, pp. 57-59, vol. 32, No. 02.
Liu Xiajin et al., "Optimization of preparation process, determination of active constituents and investigation of anti-bacterial effects for microemulsion gel of essential oils from *Chrysanthemum morifolium* stems and leaves", Chinese Traditional Patent Medicine, Jun. 2023, pp. 1766-1773, vol. 45, No. 6.
Ji Lilian et al., "Studies on the Anti-pathogenic Activities and Effective Components of the Leaves and Stalks from *Chrysanthemum nankingense* Hand. Mazz", Food Science, 2004, pp. 74-77, vol. 25, No. 9.
CNIPA, Notification of a First Office Action for CN202311456151. 3, May 29, 2024.
Chuzhou University (Applicant), Replacement claims (allowed) of CN202311456151.3, Jul. 12, 2024.
CNIPA, Notification to grant patent right for invention in CN202311456151.3, Jul. 17, 2024.

* cited by examiner

*Primary Examiner* — Susan Hoffman
(74) *Attorney, Agent, or Firm* — Hemisphere Law, PLLC; Zhigang Ma

(57) ABSTRACT

An essential oil of stems and leaves of Chuzhou chrysanthemum and its applications are provided. The essential oil is prepared by: taking and crushing fresh stems and leaves of the Chuzhou chrysanthemum by a crusher; putting the crushed stems and leaves into an extraction kettle, adding deionized water according to a ratio of 1:4 to 1:6, sealing, and connecting a cooling reflux and essential oil collection device; heating and starting counting when boiling, performing distillation extraction; then standing for cooling to room temperature, naturally layering the essential oil and water, discharging the water at a lower layer, and collecting the essential oil at an upper layer; and placing the essential oil in a brown bottle, adding anhydrous sodium sulfate to absorb water to obtain the essential oil of the stems and leaves of Chuzhou chrysanthemum.

1 Claim, 2 Drawing Sheets

ESSENTIAL OIL OF STEMS AND LEAVES OF *CHUZHOU CHRYSANTHEMUM* AND APPLICATION THEREOF

CROSS-REFERENCE TO RELATED APPLICATION

This application claims priority to Chinese Patent Application No. 202311456151.3, filed Nov. 3, 2023, which is herein incorporated by reference in its entirety.

TECHNICAL FIELD

The disclosure relates to the technical field of natural extracts, and more particularly to an essential oil of stems and leaves of Chuzhou chrysanthemum and an application thereof.

BACKGROUND

*Chrysanthemum morifolium* cv. Chuju (also referred to as Chuzhou chrysanthemum), also known as "white chrysanthemum", ranks first among the four famous chrysanthemums in China and is a national geographical indication product. Among the four famous chrysanthemums, Chuzhou chrysanthemum has the best efficacy, which can be used as a health tea drink and can also be directly used as medicine. The main producing areas of Chuzhou chrysanthemum are located in Quanjiao, Langya and Nanqiao and other areas of Chuzhou City, Anhui Province, China, with a long planting history. According to records, Ouyang Xiu, a writer in the Song Dynasty, used Chuzhou chrysanthemum flowers as a tea drink when he was a satrap in Chuzhou. During the Guangxu period of the Qing Dynasty, Chuzhou chrysanthemum was listed as a tribute, hence the name "Chuzhou tribute chrysanthemum (also referred to as Chu Gong Ju)".

According to records of traditional Chinese medicine, Chuzhou chrysanthemum has the effects of dispersing wind, clearing heat, improving eyesight and detoxifying, and can treat headache, dizziness, red eyes, chest and heart irritation, furuncle and toxic swelling. *Shennong's Classic of Materia Medica* records that the Chuzhou chrysanthemum is effective for dispelling various winds, alleviating dizziness and swelling pain, preventing the eyes from protruding, stopping tears, rejuvenating the skin, combating rheumatism and arthralgia, and benefiting blood circulation. *Supplementary Records of Famous Physicians* records that the Chuzhou chrysanthemum treats recurrent and indistinct lumbar pain, eliminates restlessness and heat in the chest, soothes the stomach and intestines, benefits the five meridians, and harmonizes the limbs. *Treatise on the Nature of Medicines* records that the Chuzhou chrysanthemum can treat symptoms of heat-induced headwind, such as dizziness leading to falling to the ground, and pain in the skull, and can dissipate various winds throughout the body. *Rihuazi Materia Medica* records that the Chuzhou chrysanthemum can promote blood circulation, treat migratory wind in the limbs, relieve restlessness of the heart and resolve stuffiness in the chest and diaphragm, treat carbuncle and toxin, headache, and improve eyesight by using the Chuzhou chrysanthemum in a pillow. *Elaboration on the Materia Medica* records that the Chuzhou chrysanthemum is specially used to treat wind heat in the head and eyes, and now it is often collected and made into pillows. *Medicinal Identification* records that the Chuzhou chrysanthemum mainly improves eyesight and hearing, eliminates restlessness and heat in the chest, and also treats dizziness and headaches. Modern pharmacological research indicates that chrysanthemums contain volatile oils, organic acids, polyphenols, flavonoids, polysaccharides, trace elements, and other active components, which possess a variety of pharmacological effects including anti-tumor, immune regulation, and antioxidation.

At present, the Chuzhou chrysanthemum industry has initially formed an industrial chain focusing on production, circulation, processing and consumption. In recent years, the Chuzhou chrysanthemum industry has shown a rapid development trend, thus promoting the market value and efficiency of Chuzhou chrysanthemum products. It is one of only three special agricultural products in Anhui province, China. The development of Chuzhou chrysanthemum has become a characteristic industrial product that helps to promote the brand of Chuzhou chrysanthemum.

Currently, the existing research mainly focuses on Chuzhou chrysanthemum breeding, Chuzhou chrysanthemum pest control, composition and function of Chuzhou chrysanthemum flower, and related products mainly focus on Chuzhou chrysanthemum flower. However, there are few reports on the stem and leaf research of Chuzhou chrysanthemum, especially on the development of related products. The preliminary research of the project team found that the contents of total phenols and total flavonoids in the leaves of Chuzhou chrysanthemum are significantly higher than those in the flowers of Chuzhou chrysanthemum. The high-performance liquid chromatography (HPLC) fingerprint spectra study shows that the leaves of Chuzhou chrysanthemum are highly similar to the flowers of Chuzhou chrysanthemum, indicating that the leaves of Chuzhou chrysanthemum had the same development and utilization value as the flowers of Chuzhou chrysanthemum. In addition, the leaves of Chuzhou chrysanthemum had a stronger special aroma than the flowers of Chuzhou chrysanthemum, which is suitable as a raw material for extraction of essential oil.

Essential oil is a kind of substance with strong aroma, which is formed by secondary metabolites in aromatic plants. It has the characteristics of changeable nature, natural source and complex composition. The essential oil can be used for skin care (cosmetic) products, which has the effect of moisturizing skin. The essential oil can enhance skin hydration, improve the composition and structure of dermis, effectively lock skin moisture, and make skin moist and elastic. In addition, the skin care products added with the essential oil also have good moisturizing effect, which can effectively soothe the skin, improve the skin elasticity, and relieve the skin pain. With the continuous development of the cosmetics industry, people have more preferences for cosmetics containing the essential oil. Moreover, the essential oil also has good sunscreen effect, anti-aging, whitening and other effects, showing a good application prospect in the field of cosmetics. Furthermore, the essential oil can be used as a natural preservative for food because of its good antimicrobial and bacteriostatic activities. Besides, the essential oil contains a variety of antioxidant components, which has good antioxidant properties and can effectively prevent the damage caused by oxidation. As a plant extract, essential oil has been widely used in food preservation, skin cosmetics, hair cosmetics, pharmaceuticals and other fields because of its various biological activities, and has shown broad application prospects in many fields.

In the disclosure, the stems and leaves of Chuzhou chrysanthemum were used as raw materials, the essential oil was extracted from the stems and leaves of Chuzhou chrysanthemum, the chemical composition and the antioxidation and antimicrobial properties of the essential oil were analyzed, and the application range of the essential oil was expanded. It provides a research and theoretical basis for the utilization of the stems and leaves of Chuzhou chrysanthemum, as well as a theoretical and experimental foundation for the deep processing and comprehensive development of geographical indication products related to Chuzhou chrysanthemum. This is beneficial for enhancing and extending the industrial chain of Chuzhou chrysanthemum, and for improving the level of production and product research and development in this area.

SUMMARY

In view of the above technical problems, the purpose of the disclosure is to provide an essential oil from stems and leaves of Chuzhou chrysanthemum and its application. With the stems and leaves of Chuzhou chrysanthemum as raw materials, the effective increment of the stems and leaves of Chuzhou chrysanthemum is realized, and its application value of the stems and leaves of Chuzhou chrysanthemum is improved. The essential oil from the stems and leaves of Chuzhou chrysanthemum can be used as fruit and vegetable preservatives, cosmetics and skin care products, and antimicrobial and bactericidal drugs. This is beneficial for improving and extending the Chuzhou chrysanthemum industrial chain, improving the level of production and product research and development of Chuzhou chrysanthemum, enriching the types of Chuzhou chrysanthemum products, and strengthening the Chuzhou chrysanthemum characteristic industry.

Technical solutions of the disclosure are as follows. Specifically, in an aspect, an essential oil of stems and leaves of Chuzhou chrysanthemum is provided.

In another aspect, a preparation method of the essential oil of the stems and leaves of Chuzhou chrysanthemum is provided, including the following steps:
  S1: taking fresh stems and leaves of Chuzhou chrysanthemum and crushing the fresh stems and leaves of Chuzhou chrysanthemum by a crusher;
  S2: putting the crushed stems and leaves of Chuzhou chrysanthemum into an extraction kettle, adding deionized water according to a ratio of the crushed stems and leaves to the deionized water in a range of 1:4 to 1:6, sealing the extraction kettle, and connecting a cooling reflux and essential oil collection device to the extraction kettle;
  S3: heating the extraction kettle, starting timing when boiling, performing distillation extraction on the extraction kettle for 1.5 hours (h) to 2.5 h to end distillation;
  S4: standing the extraction kettle for cooling to room temperature, naturally layering the essential oil and water, discharging the water at a lower layer, and collecting the essential oil at an upper layer; and
  S5: placing the essential oil at the upper layer in a brown bottle, adding anhydrous sodium sulfate to absorb water to obtain the essential oil of the stems and leaves of Chuzhou chrysanthemum, and storing in a refrigerator at 4° C. for later use.

In an embodiment, the stems and leaves of Chuzhou chrysanthemum are from Chuzhou chrysanthemum produced in Chuzhou, Anhui province, China.

In an embodiment, conditions of the crushing in the step S1 include: 18.5 kilowatts (kW) of power and 1400 revolutions per minute (r/min) of rotational speed.

In still another aspect, an application of the essential oil of the stems and leaves of Chuzhou chrysanthemum in inhibiting or killing activities of *Fusarium sulawesiensis* and *Aspergillus niger* is provided.

In even still another aspect, an application of the essential oil of the stems and leaves of Chuzhou chrysanthemum in antimicrobial and anti-inflammatory products is provided.

In an embodiment, the antimicrobial and anti-inflammatory products include fruit and vegetable preservatives, food preservatives, skin care products and cosmetics, washing products, and antimicrobial and bacteriostatic drugs.

Beneficial effects of the disclosure are as follows.

1. The inhibitory effects of the essential oil of the stems and leaves of Chuzhou chrysanthemum on *Escherichia coli* and *Staphylococcus aureus* show a good dose-response relationship. When the concentration is 100 milligrams per milliliter (mg/mL), the inhibitory rate of *Escherichia coli* is 60.73%, and the inhibitory rate of *Staphylococcus aureus* is 62.64%.

2. The inhibitory effects of the essential oil of the stems and leaves of Chuzhou chrysanthemum on *Fusarium sulawesiensis* and *Aspergillus niger* also show a good dose-response relationship. When the concentration of the essential oil is 100 micrograms per milliliter (μg/mL), the inhibitory rates on *Fusarium sulawesiensis* and *Aspergillus niger* reach 88.98% and 65.25%, respectively.

3. When the concentration of the essential oil of the stems and leaves of Chuzhou chrysanthemum in the disclosure is in the range of 0.625-20 mg/mL, the scavenging rates of hydroxyl free radical, 2,2-diphenyl-1-(2,4,6-trinitrophenyl) hydrazyl (DPPH) free radical and 2,2'-Azinobis-(3-ethylbenzothiazoline-6-sulfonate) (ABTS) free radical increase with the increase of the concentration of the essential oil, showing a good dose-response relationship. When the concentration of the essential oil of the stems and leaves of Chuzhou chrysanthemum is 20 mg/mL, the scavenging rates of three free radicals reach the maximum, which are 55.11%, 44.64%, and 84.05%, respectively. The scavenging effect of the essential oil of the stems and leaves of Chuzhou chrysanthemum on the ABTS free radical is the strongest, followed by the scavenging effect on the hydroxyl free radical.

4. In the disclosure, the stems and leaves of Chuzhou chrysanthemum are used as raw materials, the effective increment of the stems and leaves of Chuzhou chrysanthemum is realized, and its application value of the stems and leaves of Chuzhou chrysanthemum is improved. It provides research and theoretical basis for the resource utilization of the stems and leaves of Chuzhou chrysanthemum, and also provides theoretical and experimental basis for the deep processing and comprehensive development and utilization of geographical indication products Chuzhou chrysanthemum.

In addition, the disclosure develops new applications of the essential oil of the stems and leaves of Chuzhou chrysanthemum, which has significant effects in anti-inflammatory and antimicrobial properties, and antioxidation and free radical scavenging abilities. It can be used as fruit and vegetable preservative, cosmetics and skin care products, and antimicrobial and bacteriostatic drugs, etc.

DETAILED DESCRIPTION OF EMBODIMENTS

The disclosure provides an essential oil of stems and leaves of Chuzhou chrysanthemum and its application. In order to make the purpose, technical solution and effect of the disclosure clearer and more definite, the disclosure will be further described in detail below in conjunction with the embodiments. It should be understood that the embodiments described herein are merely illustrative of the disclosure and are not intended to limit the disclosure.

Embodiment 1

Specifically, a preparation method of the essential oil of the stems and leaves of Chuzhou chrysanthemum is provided, including the following steps.

S1: fresh stems and leaves of Chuzhou chrysanthemum from Chuzhou are collected and crushed by a crusher. The crushing conditions include 18.5 kW of power and 1400 r/min of rotational speed.

S2: the crushed stems and leaves of Chuzhou chrysanthemum are put into an extraction kettle, deionized water is added according to a ratio of the crushed stems and leaves to the deionized water of 1:5, the extraction kettle is sealed with a cover, and a cooling reflux and essential oil collection device is connected.

S3: the extraction kettle is started to heat, timing is started when boiling, and distillation extraction is performed on the extraction kettle for 2.5 h to end distillation.

S4: the extraction kettle is stood for cooling to room temperature, the essential oil and water are naturally layered, the water at a lower layer is discharged, and the essential oil at an upper layer is collected.

S5: the essential oil at the upper layer is placed in a brown bottle, anhydrous sodium sulfate is added to absorb water to obtain the essential oil of the stems and leaves of Chuzhou chrysanthemum, and the essential oil is stored in a refrigerator at 4° C. for later use.

Embodiment 2

Chemical composition analysis of the essential oil of the stems and leaves of Chuzhou chrysanthemum is analyzed as follows.

1. Gas Chromatography-Mass Spectrometry (GC-MS)

The essential oil of the stems and leaves of Chuzhou chrysanthemum is diluted to 100 milligrams per liter (mg/L) with n-hexane, and 1 microliter (μL) is injected into a GC-MS detector (Agilent 8890-5977B GC-MS), using an HP-5 MS ultra-inert capillary column (Agilent) with 30×0.25 millimeters (mm), inner diameter (i.d), 0.25 micrometers (μm). The inlet temperature is set to 250° C., with helium as carrier gas at a flow rate is 1.0 milliliter per minute (mL/min).

Heating procedures are as follows: the initial temperature is 50° C. and is kept for 5 min, and the temperature is raised to 110° C. at 3° C./min; the temperature is raised to 140° C. at 2° C./min and is kept for 3 min; and the temperature is raised to 260° C. at 12° C./min and is kept for 5 min, with a total time of 55 min. The inlet temperature is 250° C., the carrier gas is high purity helium (>99.999%), the constant flow rate is 1.0 mL/min, the split ratio is 100:1, the solvent delay is 3 min, and the injection volume is 1.0 μL.

Figure 1:
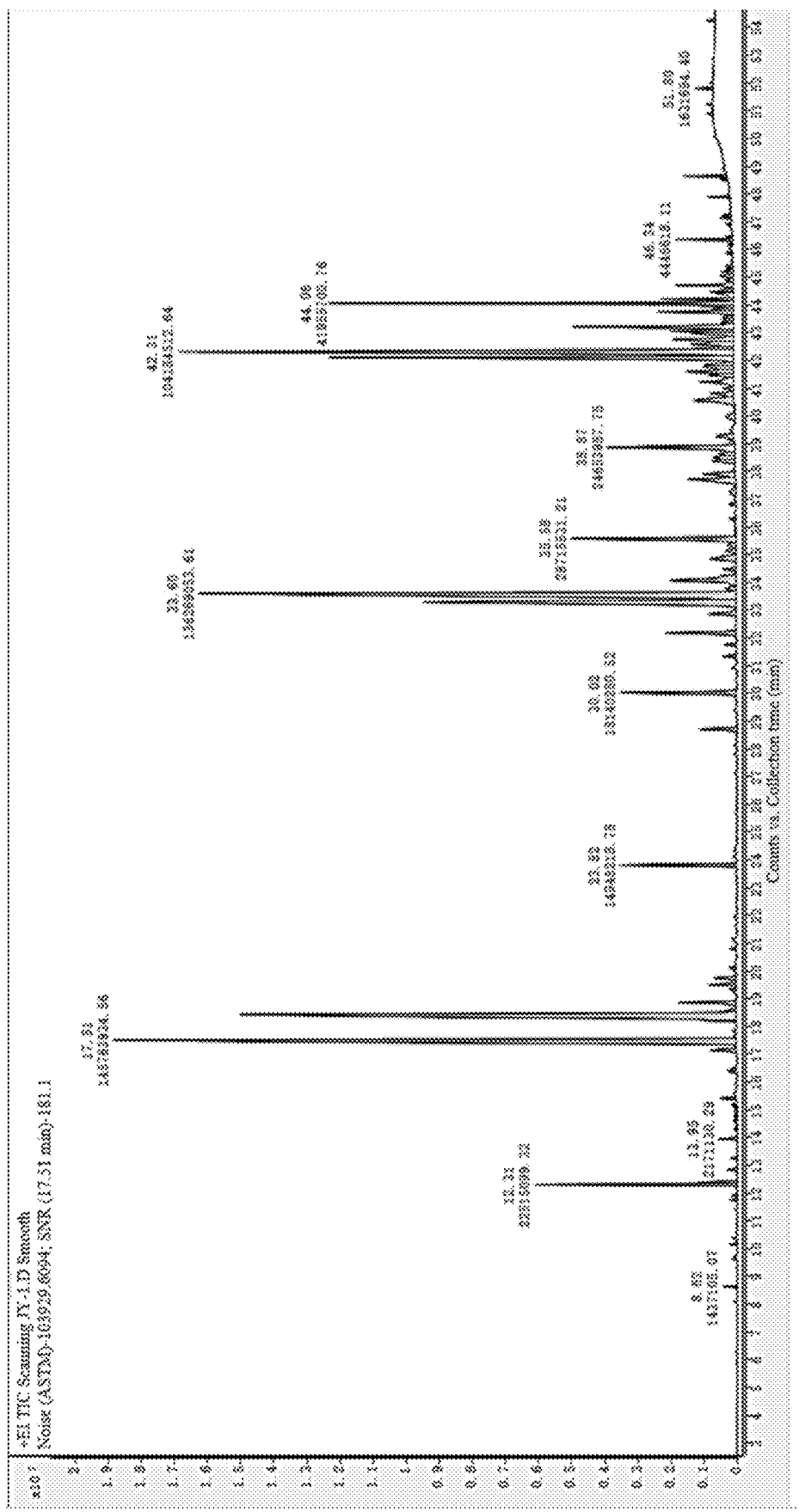
FIG. 1 illustrates a total ion current (TIC) chromatogram of the essential oil of stems and leaves of Chuzhou chrysanthemum of the disclosure analyzed by gas chromatography-mass spectrometry (GC-MS).
Figure 2:
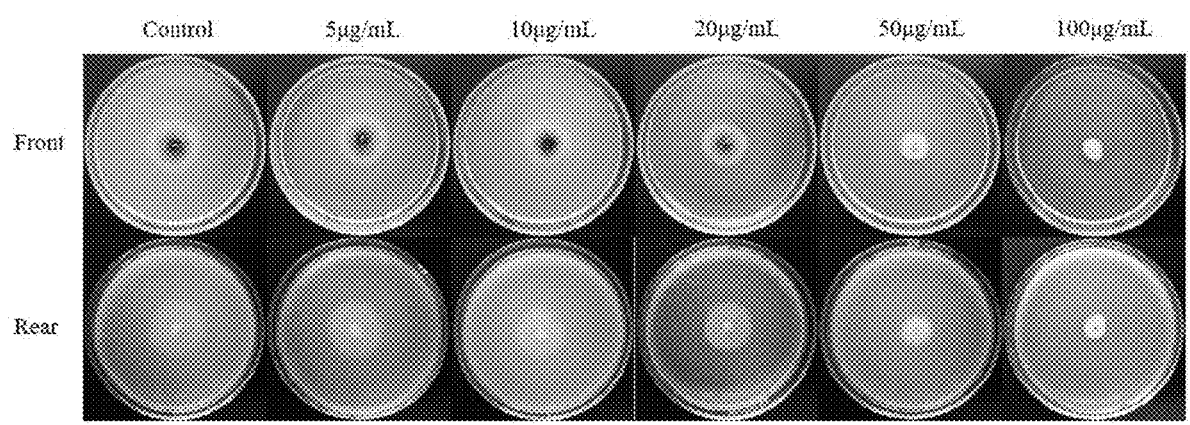
FIG. 2 illustrates inhibitory effects of the essential oil of the stems and leaves of Chuzhou chrysanthemum on *Aspergillus niger* (on the 8th day, isolated from strawberry).
Figure 3:
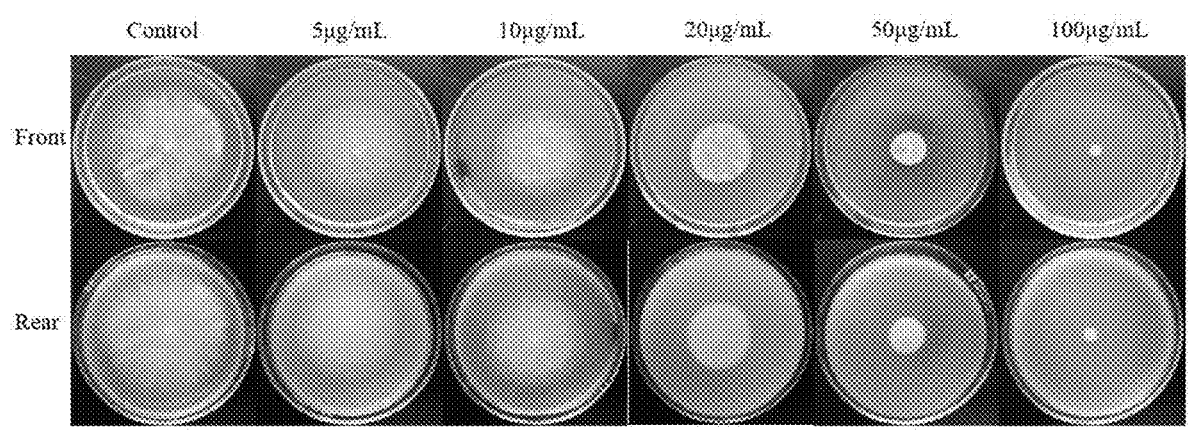
FIG. 3 illustrates inhibitory effects of the essential oil of the stems and leaves of Chuzhou chrysanthemum on *Fusarium sulawesiensis* (on the 8th day, isolated from crisp melon).

Electron impact (EI) ion source, ion source temperature 230° C., quadrupole 150° C., transmission line 230° C.; electron impact energy: 70 electron volts (eV); scanning mode: full scanning, with a mass scanning range of 50-550 mass-to-charge (m/z). The n-alkane mixed standard is diluted to 5 mg/L with n-hexane, and put in an automatic injection bottle with an injection volume of 1 μL (the TIC chromatogram is shown in FIG. 1).

2. Identification of Compounds

Identification of individual compounds is based on calculated retention index (RI) and comparison of their mass spectra with those of reference compounds available in National Institute of Standards and Technology (NIST) 20 database. The threshold matching ratio is set to 90. Under the same operating conditions, the RI related to the homologous series of n-alkanes (C7-C30) is calculated. The chemical composition of the essential oil of the stems and leaves of Chuzhou chrysanthemum is shown in Table 1 below.

TABLE 1

Analysis of chemical components of the essential oil of the stems and leaves of Chuzhou *chrysanthemum*

| Number | Retention time | Compound name | CAS | RI | Relative content |
|---|---|---|---|---|---|
| 1 | 8.62 | (1S,4R)-(−)-Camphene | 5794-04-7 | 943 | 0.10 |
| 2 | 12.31 | Eucalyptol | 470-82-6 | 1035 | 1.70 |
| 3 | 12.39 | (E)-3,7-dimethylocta-1,3,6-triene | 3779-61-1 | 1036 | 0.26 |
| 4 | 12.84 | Ocimenec | 13877-91-3 | 1047 | 0.10 |
| 5 | 13.26 | γ-terpinene | 99-85-4 | 1056 | 0.24 |
| 6 | 15.41 | cis-4-thujanol | 546-79-2 | 1105 | 0.15 |
| 7 | 16.38 | (1S,4R)-1-methyl-4-prop-1-en-2-ylcyclohex-2-en-1-ol | 7212-40-0 | 1126 | 0.12 |
| 8 | 16.46 | α-Camphor | 4501-58-0 | 1128 | 0.06 |
| 9 | 17.15 | (E)-Carveol | 547-61-5 | 1143 | 0.34 |
| 10 | 17.51 | Bornan-2-one (also referred to as D-camphor) | 464-49-3 | 1150 | 12.13 |
| 11 | 18.22 | Pinocarvone | 30460-92-5 | 1166 | 0.24 |
| 12 | 18.43 | Camphor | 76-22-2 | 1171 | 11.18 |
| 13 | 18.59 | 2,2,4-Trimethyl-3-cyclopentene-1-ethanol | 80514-13-2 | 1174 | 0.11 |
| 14 | 18.86 | Terpineol-4 | 562-74-3 | 1180 | 0.67 |
| 15 | 19.34 | Isocarveol | 35907-10-9 | 1190 | 0.08 |

TABLE 1-continued

Analysis of chemical components of the essential oil of the stems and leaves of Chuzhou chrysanthemum

| Number | Retention time | Compound name | CAS | RI | Relative content |
|---|---|---|---|---|---|
| 16 | 19.51 | Terpineol | 98-55-5 | 1194 | 0.28 |
| 17 | 19.74 | (−)-Myrtenol | 19894-97-4 | 1199 | 0.34 |
| 18 | 20.12 | Bornyl acetate | 124-76-5 | 1207 | 0.08 |
| 19 | 20.8 | (−)-Carvacrol | 1197-06-4 | 1222 | 0.09 |
| 20 | 23.82 | L-Born-2-yl acetate | 5655-61-8 | 1289 | 1.27 |
| 21 | 28.71 | (−)-β-elemene | 515-13-9 | 1388 | 0.49 |
| 22 | 30.02 | Caryophyllene | 87-44-5 | 1414 | 1.61 |
| 23 | 31.34 | Sesquisabinene | 58319-04-3 | 1439 | 0.18 |
| 24 | 31.76 | α-caryophyllene | 6753-98-6 | 1447 | 0.16 |
| 25 | 32.18 | β-(Z)-Farnesene | 28973-97-9 | 1455 | 1.01 |
| 26 | 32.87 | Amorphadiene | 211237-38-6 | 1468 | 0.49 |
| 27 | 33.30 | γ-Amorphene | 6980-46-7 | 1476 | 6.79 |
| 28 | 33.60 | β-Selinene | 17066-67-0 | 1482 | 12.43 |
| 29 | 33.78 | 2,4-Diisopropenyl-1-methylcyclohexane | 61142-58-3 | 1485 | 0.23 |
| 30 | 34.08 | α-Cedrene | 469-61-4 | 1491 | 1.61 |
| 31 | 34.47 | β-Guaiene | 1000159-39-3 | 1498 | 0.19 |
| 32 | 34.84 | Bornyl valerate | 7549-41-9 | 1505 | 0.64 |
| 33 | 35.15 | Pseudopterosin-1-ol | 1000140-22-9 | 1511 | 0.21 |
| 34 | 35.36 | Bornyl isovalerate | 76-50-6 | 1514 | 0.18 |
| 35 | 35.58 | β-Sesquiphellandrene | 20307-83-9 | 1518 | 2.61 |
| 36 | 36.28 | (−)-Italicene ether | 104188-25-2 | 1531 | 0.10 |
| 37 | 36.81 | (E)-Sesquisabinene hydrate | 145512-84-1 | 1540 | 0.12 |
| 38 | 37.26 | β-(Z)-Curcumene-12-ol | 698365-10-5 | 1548 | 0.26 |
| 39 | 37.71 | Camphor (E)-2-methyl-2-butenoic acid | 101223-92-1 | 1557 | 1.01 |
| 40 | 37.91 | Nerolidol | 7212-44-4 | 1560 | 0.61 |
| 41 | 38.37 | Germacrene D-4-ol | 198991-79-6 | 1568 | 0.42 |
| 42 | 38.51 | (+)-Spathulenol | 6750-60-3 | 1571 | 0.44 |
| 43 | 38.65 | 1-(4-Methylphenyl)-2-methyl-3-buten-1-ol | 83173-76-6 | 1273 | 0.27 |
| 44 | 38.87 | Trans-7-epi-sesquisabinene hydrate | 1000374-17-7 | 1577 | 2.30 |
| 45 | 39.13 | Isoeudesmol | 88395-46-4 | 1582 | 0.08 |
| 46 | 39.26 | Globulol | 489-41-8 | 1584 | 0.38 |
| 47 | 39.97 | Thujopsal | 470-41-7 | 1597 | 0.29 |
| 48 | 40.56 | Cedr-13-ol | 18319-35-2 | 1613 | 1.12 |
| 49 | 40.81 | Shogaol | 58334-55-7 | 1620 | 0.43 |
| 50 | 41.00 | Bisoprolol-1-oxide | 1000156-11-0 | 1626 | 0.17 |
| 51 | 41.23 | Trans-longifolinol | 1000159-36-5 | 1633 | 1.08 |
| 52 | 41.59 | Caryophyll-4(12),8(13)-diene-5α-ol | 19431-80-2 | 1643 | 0.76 |
| 53 | 41.77 | (+)-Ledene | 21747-46-6 | 1649 | 0.53 |
| 54 | 41.84 | Scutellarin | 66873-38-9 | 1651 | 0.50 |
| 55 | 42.11 | β-Eudesmol | 473-15-4 | 1659 | 6.00 |
| 56 | 42.31 | Neodihydrotheasperin | 5945-72-2 | 1665 | 9.73 |
| 57 | 42.42 | Trans-torreya alcohol | 39599-18-3 | 1668 | 0.51 |
| 58 | 42.58 | β-Caryophyllene alcohol | 77171-55-2 | 1673 | 0.70 |
| 59 | 42.76 | Epiglobulol | 88728-58-9 | 1678 | 1.07 |
| 60 | 42.97 | Octahydro-tetramethyl-cyclopropa-azulene-ketone | 34413-94-0 | 1685 | 0.56 |
| 61 | 43.06 | Levomecol | 23089-26-1 | 1687 | 0.72 |
| 62 | 43.21 | α-Bisabolol | 515-69-5 | 1692 | 2.22 |
| 63 | 43.35 | Allo-aromadendrene oxide-(1) | 1000156-12-8 | 1696 | 0.14 |
| 64 | 43.47 | Parthenolide | 20554-84-1 | 1700 | 0.13 |
| 65 | 43.55 | 14-Hydroxycaryophyllene | 50277-33-3 | 1704 | 0.14 |
| 66 | 43.74 | Ledene oxide | 1000159-36-7 | 1715 | 0.90 |
| 67 | 43.84 | Bicyclo[11.3.0]hexadecane-2,14-dione | 1000196-24-4 | 1720 | 0.21 |
| 68 | 43.95 | Matricin | 529-05-5 | 1727 | 0.29 |
| 69 | 44.06 | Isododecane epoxide | 1000159-36-6 | 1733 | 3.89 |
| 70 | 44.21 | α-Cyperone | 473-08-5 | 1741 | 0.57 |
| 71 | 44.41 | Calamenene epoxide | 1000151-46-0 | 1753 | 0.21 |
| 72 | 44.47 | Cedrone | 108645-54-1 | 1756 | 0.18 |
| 73 | 44.71 | Allo-aromadendrene oxide-(2) | 1000156-12-7 | 1769 | 0.72 |
| 74 | 44.89 | Achilleolide | 38022-97-8 | 1780 | 0.09 |
| 75 | 45.05 | Humuleneol-II | 19888-00-7 | 1789 | 0.30 |
| 76 | 45.29 | Eudesmene oxide-(1) | 1000151-98-4 | 1803 | 0.07 |
| 77 | 45.40 | Isolongifolol | 1139-17-9 | 1812 | 0.11 |
| 78 | 45.86 | (+/−)-Phytone | 502-69-2 | 1847 | 0.08 |
| 79 | 45.91 | Oxacyclotetradeca-4,11-diyne | 6568-32-7 | 1851 | 0.06 |
| 80 | 46.34 | 1,4,9-Tridecenylbenzene | 13393-63-0 | 1884 | 0.41 |
| 81 | 46.46 | Linolenic acid | 463-40-1 | 1894 | 0.05 |
| 82 | 47.13 | Geranyl-α-terpinene | 1000374-18-8 | 1956 | 0.10 |

TABLE 1-continued

Analysis of chemical components of the essential oil
of the stems and leaves of Chuzhou chrysanthemum

| Number | Retention time | Compound name | CAS | RI | Relative content |
|---|---|---|---|---|---|
| 83 | 47.23 | Palmitic acid | 57-10-3 | 1965 | 0.09 |
| 84 | 47.90 | Falcarinol | 21852-80-2 | 2033 | 0.18 |
| 85 | 48.55 | Methyl linoleate | 301-00-8 | 2104 | 0.05 |
| 86 | 48.64 | Phytol | 150-86-7 | 2114 | 0.28 |

As can be seen from Table 1, 86 components are detected in the essential oil of the stems and leaves of Chuzhou chrysanthemum. The contents of β-selinene (12.43%), bornan-2-one (12.13%), camphor (11.18%), neodihydrotheasperin (9.73%), γ-amorphaene (6.79%) and β-eudesmol (6.00%) are more than 5%, which accounted for 58.26% of the total content of the essential oil, which are the main components of the essential oil of the stems and leaves of Chuzhou chrysanthemum.

Embodiment 3

Antimicrobial Activity Assay
1. Bacterial Inhibition Assay

Cultured *Escherichia coli* and *Staphylococcus aureus* are diluted into 106 colony forming units per milliliter (CFU/mL) bacterial solution respectively, and evenly spread on a potato dextrose agar (PDA) plate. After standing for 10 min, the filter paper with a diameter of 6 mm made by a punch is spread on the PDA plate, and 6 pieces are evenly placed in each plate. 10 μL of essential oil of stems and leaves of Chuzhou chrysanthemum with a concentration of 5 mg/mL is added with a pipette, and the culture dish is placed in a 37° C. incubator for culture. In the same way, the bacterial inhibition assay of the essential oil of the stems and leaves of Chuzhou chrysanthemum is carried out at the concentrations of 10, 20, 50, and 100 mg/mL. After 16 to 18 h of incubation, a diameter of a bacteriostatic ring (including the piece) is measured with a vernier caliper and recorded. When measuring the bacteriostatic ring, the bacteriostatic ring with uniform and completely sterile growth should be selected, and its diameter should be measured with an outer edge of the bacteriostatic ring as the boundary. Six parallel experiments are performed for each concentration, and the mean and standard deviation are calculated. Ethyl acetate is used as blank control, and streptomycin sulfate and ampicillin are used as positive controls.

TABLE 2

Inhibitory effects of the essential oil of stems and leaves of Chuzhou chrysanthemum on *Escherichia coli* and *Staphylococcus aureus*

| | *Escherichia coli* | | *Staphylococcus aureus* | |
|---|---|---|---|---|
| Concentration (mg/mL) | Bacteriostatic ring diameter (mm) | Inhibitory rate (%) | Bacteriostatic ring diameter (mm) | Inhibitory rate (%) |
| Ethyl acetate (control) | 7.73 ± 0.33E | — | 7.73 ± 0.33G | — |
| 5 | 8.65 ± 0.36E | 10.51 ± 3.69F | 8.48 ± 0.31G | 8.72 ± 3.37G |
| 10 | 10.82 ± 0.66D | 28.37 ± 4.19E | 11.44 ± 0.84F | 32.11 ± 5.11F |
| 20 | 15.2 ± 1.35C | 48.83 ± 4.36D | 12.92 ± 0.63E | 40.03 ± 2.87E |
| 50 | 17.77 ± 1.41B | 56.26 ± 3.63B | 15.15 ± 0.66D | 48.89 ± 2.21D |
| 100 | 19.70 ± 0.54A | 60.73 ± 1.09A | 20.75 ± 1.13A | 62.64 ± 2.08A |
| Streptomycin sulfate 500 ppm | 15.98 ± 0.43C | 51.61 ± 1.3CD | 18.10 ± 0.48B | 57.27 ± 1.13B |
| Ampicillin 50 ppm | 17.12 ± 0.63B | 54.79 ± 1.66BC | 16.58 ± 1.17C | 53.2 ± 3.03C |

It can be seen from Table 2 that the diameters of the bacteriostatic ring of the essential oil of the stems and leaves of Chuzhou chrysanthemum against *Escherichia coli* and *Staphylococcus aureus* increase with the increase of the concentration of the essential oil, indicating that the inhibitory effect of the essential oil of the stems and leaves of Chuzhou chrysanthemum against the two bacteria increases with the increase of the concentration of the essential oil, showing a good dose-response relationship. When the concentration of the essential oil of the stems and leaves of Chuzhou chrysanthemum is 5 mg/mL, both *Escherichia coli* and *Staphylococcus aureus* show low sensitivity, with inhibition rates of 10.51% and 8.72% respectively. When the concentration of the essential oil of the stems and leaves of Chuzhou chrysanthemum is 20 mg/mL, *Escherichia coli* and *Staphylococcus aureus* show moderate sensitivity, with inhibition rates of 48.83% and 40.03% respectively. When the concentration of the essential oil of the stems and leaves of Chuzhou chrysanthemum is 50 mg/mL, *Escherichia coli* and *Staphylococcus aureus* show high sensitivity, with inhibition rates of 56.26% and 48.89% respectively. When the concentration of the essential oil of the stems and leaves of Chuzhou chrysanthemum is 100 mg/mL, the diameter of the bacteriostatic ring of *Staphylococcus aureus* is 20.75 mm, greater than 20 mm, and the inhibition effect is extremely sensitive, with an inhibition rate of 62.64%.

2. Fungal Inhibition Assay

The antimicrobial activity of the essential oil of stems and leaves of Chuzhou chrysanthemum against *Fusarium sulawesiensis* and *Aspergillus niger* is determined by growth rate method. When the PDA culture media are cooled to about 50° C., the essential oils of stems and leaves of Chuzhou chrysanthemum are added respectively, immediately shaken, poured into five 90 mm Petri dishes to prepare plates with different concentrations of essential oils of 5 µg/mL, 10 µg/mL, 20 µg/mL, 50 µg/mL and 100 µg/mL, respectively. Using a sterilized punch with an inner diameter of 3 mm, the mycelial block is punched on the cultured flat plate media of *Fusarium sulawesiensis* and *Aspergillus niger*, the mycelial block is stuck upside down on the flat plate media with tweezers, cultured in an incubator at 25° C. for 8 days, and the colony diameter is measured by a cross method.

TABLE 3

Inhibitory effects of the essential oil of stems and leaves of Chuzhou *chrysanthemum* on *Fusarium sulawesiensis* and *Aspergillus niger*

| Concentration (µg/mL) | *Fusarium sulawesiensis* | | *Aspergillus niger* | |
|---|---|---|---|---|
| | Colony diameter (mm) | Inhibitory rate (%) | Colony diameter (mm) | Inhibitory rate (%) |
| Blank control | 61.39 ± 2.20A | — | 31.53 ± 0.90A | — |
| 5 | 50.37 ± 1.36B | 17.95 ± 2.21E | 29.55 ± 0.44B | 6.27 ± 1.39E |
| 10 | 48.02 ± 0.62C | 21.78 ± 1.01D | 26.29 ± 0.79C | 16.61 ± 2.51D |
| 20 | 31.70 ± 1.26D | 48.37 ± 2.06C | 24.65 ± 0.93D | 21.80 ± 2.95C |
| 50 | 19.41 ± 2.26E | 68.39 ± 3.68B | 20.61 ± 1.78E | 34.61 ± 5.64B |
| 100 | 6.76 ± 0.75F | 88.98 ± 1.23A | 10.96 ± 1.44F | 65.25 ± 4.58A |

It can be seen from Table 3 that the colony diameters of *Fusarium sulawesiensis* and *Aspergillus niger* decrease with the increase of the concentration of the essential oil of the stems and leaves of Chuzhou chrysanthemum, indicating a good dose-response relationship in the inhibitory effect of the essential oil on the two fungi. Moreover, the inhibitory effect of the essential oil of the stems and leaves of Chuzhou chrysanthemum on *Fusarium sulawesiensis* is significantly stronger than that on *Aspergillus niger*. When the concentration of the essential oil of the stems and leaves of Chuzhou chrysanthemum is 20 g/mL, the inhibition rate of *Fusarium sulawesiensis* is 48.37%, while that of *Aspergillus niger* is only 21.80%. When the concentration of the essential oil of the stems and leaves of Chuzhou chrysanthemum is 50 g/mL, the inhibition rate of *Fusarium sulawesiensis* is 68.39%, while that of *Aspergillus niger* is 34.61%. When the concentration of the essential oil of the stems and leaves of Chuzhou chrysanthemum is 100 µg/mL, the inhibition rate of *Fusarium sulawesiensis* is 88.98%, while that of *Aspergillus niger* is 65.25%.

Embodiment 4

Determination of Antioxidation Activity

1. Determination of Hydroxyl Free Radical (—OH) Scavenging Ability 1 mL of essential oil solutions with different concentrations (0.625 mg/mL, 1.25 mg/mL, 2.5 mg/mL, 5 mg/mL, 10 mg/mL, 20 mg/mL) and 1 mL of 6 millimoles per liter (mmol/L) of $FeSO_4$ solution are put into each test tube and mixed, and 1 mL of 6 mmol/L $H_2O_2$ is added after mixing well. After mixing well in the dark and standing for 10 min, 1 mL of 6 mmol/L salicylic acid solution is added, and reacted in water bath at 37° C. for 30 min. After taking it out, the absorbance is measured at 510 nanometers (nm), with ascorbic acid ($V_C$) as positive control, and the parallel measurement is repeated for 3 times. Formula: R (%)= $[(A_0-A_1)/A_0] \times 100$. For the above formula, R represents the scavenging ability, and $A_0$ represents the absorbance of the mixed solution of experimental reagent solution and 1 mL absolute ethanol; $A_i$ represents the absorbance of the mixed solution of experimental reagent solution and 1 mL sample solution.

2. Determination of DPPH Free Radical Scavenging Ability 1 mL of essential oil solutions with different concentrations (0.625 mg/mL, 1.25 mg/mL, 2.5 mg/mL, 5 mg/mL, 10 mg/mL, 20 mg/mL) and 2 mL of DPPH solution are put into each test tube and mixed, and reacted in the dark for 30 min, the absorbance is measured at 517 nm, with ethanol as the blank control and $V_C$ as positive control, and the parallel measurement is repeated for 3 times. Formula: R (%)= $[(A_0-A_1)/A_0] \times 100$. From the analysis of the above formula, it can be known that: R represents the scavenging ability, and $A_0$ represents the absorbance of the mixed solution of experimental reagent solution and 1 mL absolute ethanol; $A_i$ represents the absorbance of the mixed solution of experimental reagent solution and 1 mL sample solution.

3. Determination of ABTS Free Radical Scavenging Ability 1 mL of essential oil solutions with different concentrations (0.625 mg/mL, 1.25 mg/mL, 2.5 mg/mL, 5 mg/mL, 10 mg/mL, 20 mg/mL) and 2 mL of ABTS solution are put into each test tube and mixed, and reacted in the dark for 30 min, the absorbance is measured at 734 nm, with ethanol as the blank control and $V_C$ as positive control, and the parallel measurement is repeated for 3 times. Formula: R (%)= $[(A_0-A_1)/A_0] \times 100$. From the analysis of the above formula, it can be known that: R represents the scavenging ability, and $A_0$ represents the absorbance of the mixed solution of experimental reagent solution and 1 mL absolute ethanol; $A_i$ represents the absorbance of the mixed solution of experimental reagent solution and 1 mL sample solution.

TABLE 4

Antioxidation activity of the essential oil of the stems and leaves of Chuzhou *chrysanthemum*

| Concentration (mg/mL) | Scavenging ability of hydroxyl free radical | Scavenging ability of DPPH free radical | Scavenging ability of ABTS free radical |
|---|---|---|---|
| 0.625 | 18.74 ± 1.89F | 19.99 ± 1.66F | 18.14 ± 1.32F |
| 1.25 | 27.22 ± 1.15E | 24.10 ± 1.33E | 36.21 ± 1.91E |
| 2.5 | 34.66 ± 1.08D | 28.37 ± 1.13D | 44.90 ± 1.86D |
| 5 | 38.57 ± 1.28C | 33.88 ± 1.15C | 71.94 ± 1.65C |
| 10 | 46.39 ± 1.45B | 38.67 ± 1.39B | 87.54 ± 1.44B |
| 20 | 55.11 ± 1.60A | 44.64 ± 1.85A | 94.05 ± 0.72A |

When the concentration of the essential oil of the stems and leaves of Chuzhou chrysanthemum in the disclosure is in the range of 0.625-20 mg/mL, the scavenging rates of hydroxyl free radical, DPPH free radical and ABTS free radical increase with the increase of the concentration of the essential oil, showing a good dose-response relationship. When the concentration of the essential oil of the stems and leaves of Chuzhou chrysanthemum is 20 mg/mL, the scavenging rates of three free radicals reach the maximum, which are 55.11%, 44.64%, and 84.05%, respectively. The scavenging effect of the essential oil of the stems and leaves of Chuzhou chrysanthemum on the ABTS free radical is the strongest, followed by the scavenging effect on the hydroxyl free radical.

What is claimed is:

1. A preparation method of essential oil of stems and leaves of Chuzhou chrysanthemum;
   wherein the preparation method of the essential oil of the stems and leaves of the Chuzhou chrysanthemum comprises the following steps:
   S1: taking fresh stems and leaves of the Chuzhou chrysanthemum and crushing the fresh stems and leaves of the Chuzhou chrysanthemum by a crusher; wherein conditions of the crushing comprise: 18.5 kilowatts (kW) of power and 1400 revolutions per minute (r/min) of rotational speed;
   S2: putting the crushed stems and leaves of the Chuzhou chrysanthemum into an extraction kettle, adding deionized water according to a ratio of the crushed stems and leaves to the deionized water of 1:5, sealing the extraction kettle, and connecting a cooling reflux and essential oil collection device to the extraction kettle;
   S3: heating the extraction kettle, starting timing when boiling, performing distillation extraction on the extraction kettle for 2.5 hours (h) to end distillation;
   S4: standing the extraction kettle for cooling to room temperature, naturally layering the essential oil and water, discharging the water at a lower layer, and collecting the essential oil at an upper layer; and
   S5: placing the essential oil in a brown bottle, adding anhydrous sodium sulfate to absorb water to obtain the essential oil of the stems and leaves of the Chuzhou chrysanthemum, and storing in a refrigerator at 4° C. for later use; and
   wherein main components of the essential oil of the stems and leaves of the Chuzhou chrysanthemum comprise: β-selinene accounting for 12.43%, bornan-2-one accounting for 12.13%, camphor accounting for 11.18%, neodihydrotheasperin accounting for 9.73%, γ-amorphene accounting for 6.79%, and β-eudesmol accounting for 6.00%.

* * * * *